United States Patent
Der Ovanesian

Patent Number: 6,074,415
Date of Patent: *Jun. 13, 2000

[54] HOT OR COLD APPLICATOR WITH INNER ELEMENT

[76] Inventor: Mary Der Ovanesian, 6650 Coolidges St., Hollywood, Fla. 33024

[*] Notice: This patent is subject to a terminal disclaimer.

[21] Appl. No.: 09/159,077

[22] Filed: Sep. 22, 1998

Related U.S. Application Data

[63] Continuation of application No. 08/689,899, Aug. 15, 1996, Pat. No. 5,840,080.

[51] Int. Cl.⁷ .................................................. A61F 7/00
[52] U.S. Cl. .......................... 607/114; 607/96; 607/112; 062/530
[58] Field of Search .................. 607/96–114; 62/530; 126/204; 383/901; 165/46

[56] References Cited

U.S. PATENT DOCUMENTS

| | | |
|---|---|---|
| 1,927,751 | 9/1933 | Mensi . |
| 1,964,962 | 7/1934 | Rosenblum . |
| 2,547,886 | 4/1951 | Poux . |
| 2,602,302 | 7/1952 | Poux . |
| 2,769,308 | 11/1956 | Krasno . |
| 2,800,456 | 7/1957 | Shepherd . |
| 2,984,839 | 5/1961 | Conrad et al. . |
| 3,149,943 | 9/1964 | Amador . |
| 3,191,392 | 6/1965 | Donnelly . |
| 3,429,138 | 2/1969 | Goldmerstein . |
| 3,463,161 | 8/1969 | Andrassy . |
| 3,491,761 | 1/1970 | Baker . |
| 3,500,014 | 3/1970 | Longo . |
| 3,506,013 | 4/1970 | Zdenek . |
| 3,559,416 | 2/1971 | Cornwall . |
| 3,804,077 | 4/1974 | Williams . |
| 3,871,376 | 3/1975 | Kozak ................................. 128/275.1 |
| 3,874,504 | 4/1975 | Verakas . |
| 3,951,127 | 4/1976 | Watson et al. . |
| 3,977,202 | 8/1976 | Forusz et al. . |
| 4,077,390 | 3/1978 | Stanley et al. . |
| 4,462,224 | 7/1984 | Dunshee et al. . |
| 4,573,447 | 3/1986 | Thrash et al. . |
| 4,708,812 | 11/1987 | Hatfield . |
| 4,753,241 | 6/1988 | Brannigan et al. . |
| 4,753,242 | 6/1988 | Saggers et al. . |
| 4,756,311 | 7/1988 | Francis . |
| 4,780,117 | 10/1988 | Lahey et al. . |
| 4,872,442 | 10/1989 | Manker . |
| 4,880,953 | 11/1989 | Manker . |
| 4,886,063 | 12/1989 | Crews . |
| 4,908,166 | 3/1990 | Salyer . |
| 4,910,978 | 3/1990 | Gordon et al. . |
| 4,925,603 | 5/1990 | Nambu . |
| 4,962,761 | 10/1990 | Golden ................................. 607/114 |
| 5,069,208 | 12/1991 | Noppel et al. ....................... 128/403 |
| 5,179,944 | 1/1993 | McSymytz . |
| 5,245,938 | 9/1993 | Frye . |
| 5,339,796 | 8/1994 | Manker . |
| 5,395,400 | 3/1995 | Stafford et al. . |
| 5,423,996 | 6/1995 | Salyer . |
| 5,429,762 | 7/1995 | Kitahara et al. . |
| 5,456,852 | 10/1995 | Isiguro . |
| 5,486,206 | 1/1996 | Avery ................................... 607/114 |
| 5,534,020 | 7/1996 | Cheney . |
| 5,552,075 | 9/1996 | Salyer . |
| 5,843,145 | 12/1998 | Brink ................................... 607/114 |

Primary Examiner—Linda C. M. Dvorak
Assistant Examiner—David M. Ruddy
Attorney, Agent, or Firm—Brinkley, McNerney, Morgan, Solomon & Tatum, LLP

[57] ABSTRACT

A flexible heat transfer device 1 for heating or cooling a surface such as the skin has an envelope 2 formed from two double walled sheets 3 and 4. Each sheet contains within the double wall a first high thermal capacity material 11 such as a freezing gel that is flexible when frozen for good surface contact. The space 13 between the double walls contains a second high thermal capacity material 12 that may have different physical properties than the first material. This may be in the form of a removable pouch insert 24 that may be heated or cooled separately. The device is more versatile in its applications and provides for more prolonged heating and cooling.

23 Claims, 1 Drawing Sheet

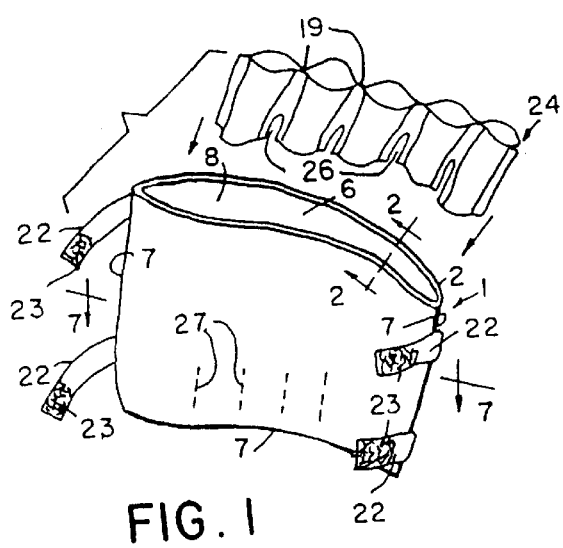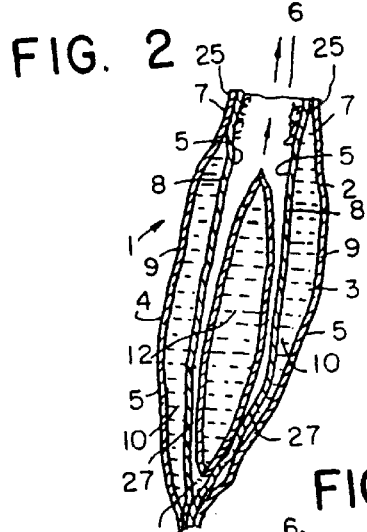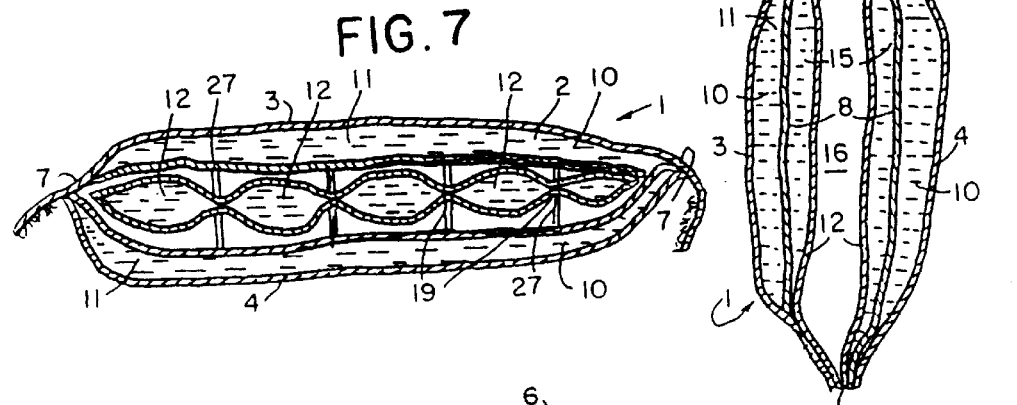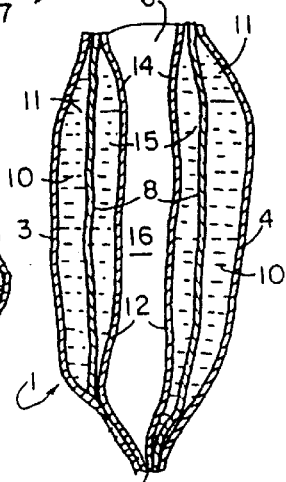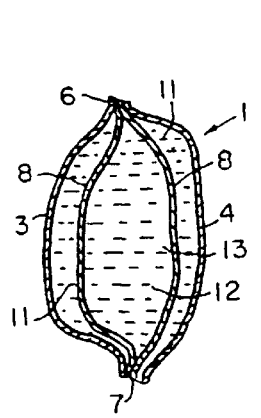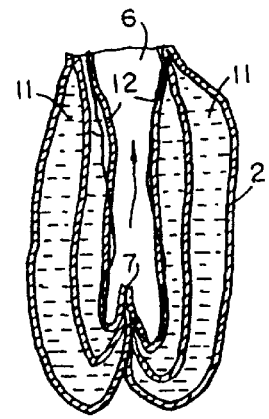

6,074,415

HOT OR COLD APPLICATOR WITH INNER ELEMENT

CROSS-REFERENCE TO RELATED APPLICATIONS

This is a continuation of prior application Ser. No. 08/689,899, filed Aug. 15, 1996, now U.S. Pat. No. 5,840,080. The entire disclosure of the prior application is considered to be part of the disclosure of the accompanying application and is hereby incorporated by reference therein.

STATEMENT REGARDING FEDERALLY SPONSORED RESEARCH OR DEVELOPMENT

N/A

BACKGROUND OF THE INVENTION

1. Field of the Invention

This invention relates Lo a reusable therapeutic device which may be used for cooling or heating and features a flexible bag which may be heated or cooled and then applied to a body part for thermal application with an inner element that enhances the thermal effects.

2. Description of Related Art

U.S. Pat. No. 4,592,358 issued Jun. 3, 1986 to Westplate provides a useful review of the patent literature in this art.

Despite the numerous advances that have been made in this art, people who need to apply heat or cold to the body for prolonged periods of time still find deficiencies in the available devices, because they don't provide relatively uniform temperature for relatively long periods of time, with the exception of the electric heating pads. When heat or cold is to be applied to the body surface, the temperature must not be so hot or cold as to be injurious or uncomfortable, while the total thermal capacity must be great enough to be therapeutically effective for a prolonged period of time.

BRIEF SUMMARY OF THE INVENTION

The invention comprises a flexible, conformable hot or cold pack having an envelope of a first high heat capacity material surrounding a second high heat capacity material for enhanced and more prolonged application of heating or cooling to any surface.

It is accordingly an object of the invention to provide a cooling and/or heating applicator that is sufficiently flexible to conform to various body parts to make surface contact for effective heat transfer.

It is another object that the applicator provide heating and/or cooling at an effective temperature for a greatly prolonged period of time for optimal therapeutic benefit.

It is another object that the device be reversible so that the surface properties may be altered in at least one alternative embodiment.

It is yet another object that the device have a removable inner portion that may be separately heated or cooled in an alternative embodiment of the invention.

These and other objects, advantages and features of the invention will become more apparent when the detailed description is studied in conjunction with the drawings, in which like elements are designated by the same reference characters in the various figures.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 1 is a perspective view of the invention with a removable refrigerant pouch ready to be inserted.

FIG. 2 is a sectional view taken through line 2—2 of FIG. 1 with pouch inserted.

FIG. 3 is a sectional view, as in FIG. 2, of another embodiment of the invention with a non-removable inner high thermal capacity material.

FIG. 4 is a sectional view, as in FIG. 2, of another embodiment of the invention with reversible inner and outer high thermal capacity materials.

FIG. 5 is a sectional view of the embodiment of FIG. 4 partially everted.

FIG. 6 is a sectional view of the embodiment of FIG. 4 completely everted.

FIG. 7 is a sectional view taken through line 7—7 of FIG. 1.

DETAILED DESCRIPTION OF THE INVENTION

Referring now first to FIGS. 1, 2 and 7, the embodiment of the invention shown here comprises a flexible heat transfer device 1 that conforms readily to the irregular surface of a body part so as to provide good surface contact for effective thermal transfer for heating or cooling. End straps 22 with hook and loop fasteners 23 permit the device to be wrapped around an arm, for example, and secured in place by the straps. The device 1 includes an outer envelope 2 formed of two double-walled sheets 3, 4 having broad faces 5. The sheets 3, 4 are joined together on 3 edges 7 and unjoined on one edge 6. Each double-walled sheet 3, 4 is formed of an inner panel 8 and an outer panel 9 sealed along all their edges 6, 7 to define therebetween a volume 10. The volumes 10 contain a first high thermal capacity material 11 such as one of the freezing gels well known in the art, such as that disclosed by U.S. Pat. No. 4,324,111 which changes state from liquid to slush at around zero degrees centigrade and requires considerable heat energy as it warms through, this change of state to serve as an artificial ice that is not rigid. U.S. Pat. No. 5,314,005 discusses other materials for this purpose including some that may be heated in a microwave oven for use as hot packs.

The envelope so formed is open at the edge 6 to permit the insertion of a flexible pouch 24. The pouch 24 and the envelope are formed of thin flexible liquid-impermeable web such as plastic film. The thickness has been exaggerated for illustrative purposes.

The pouch 24 contains a second high thermal capacity material 12. After inserting the pouch 24 through the open side 6 of the envelope into the space 13 defined by the inner panels 8, the open side 6 may be closed by a releasable closure 25 which may be hook and loop, snaps, zipper, or the like.

Multiple pouches 24 may be provided so that one is being used in the envelope while others are being chilled or heated.

The pouch 24 may be segmented as shown to make it more flexible and to maintain a flatter shape for insertion in the envelope by seams 19 sealing together the two flexible webs 14 that make up the outer wall of the pouch. The seams 19 may be provided with notches 26 that cooperate with short partitions 27 connecting the inner panels 8. This stabilizes the pouch within the envelope.

The high thermal capacity material 12 in the pouch may be identical to, or different than the material 11 in the envelope walls. It may even be rigid when frozen such as plain water, since segmentation provides some flexibility.

The materials 11 and 12 may be selected on the basis of their particular physical properties to enhance the utility of the device. Those properties include, but are not limited to, heat of fusion, heat capacity, thermal conductivity, temperature of transition from liquid to solid, rigidity in the solid phase, reaction to microwave radiation, vapor pressure and boiling point.

The term high thermal capacity material is used herein to refer to a material such as water, a freezing gel, or materials disclosed in the U.S. Pat. Nos. 5,314,005; 4,592,358; 4,324,111 that have a high heat of fusion and/or a high heat capacity such that a relatively large number of calories is required to change the temperature thereof compared to most materials. The principal ingredient in most of these high thermal capacity materials is water. Its heat of fusion, that is the amount of heat given up when going from liquid to solid or absorbed when going from solid to liquid, is 80 calories per gram. This is more than triple that of most materials. The heat capacity of water, that is the amount of heat given up or absorbed to change its temperature 1 degree centigrade is 1 calorie per gram. This is more than triple that of most materials. A high thermal capacity material is one having a heat of fusion and/or a heat capacity that are at least one half that of water.

Insulation such as foam is comprised mostly of trapped air which has a low thermal conductivity, i.e. it transmits calories poorly. Because it is a gas, it has very low density (g/cc). Consequently it has very low thermal capacity per volume of insulation.

Thermal conductivity of the material 11 is important in the rate of transfer of heat to or from the insert or pouch 24. By acting as a partial insulator, it can prolong the cooling effect and also prevent a very cold or hot insert from injuring the skin, while maintaining a relatively uniform surface temperature. The envelope 2 may also be used without the pouch, as desired.

Referring now to FIG. 3, a heat transfer device 1 is shown in which the two double-walled sheets 3, 4 are sealed an all edges 6, 7 with a sealed inner space 13 defined by the two inner panels 8 containing the second high thermal capacity material 12 and the volumes between the double walls of each sheet containing the first high thermal capacity material 11.

FIGS. 4–6 show another embodiment of the invention in which the entire device may be turned inside out like a reversible jacket. As shown in the first mode of operation in FIG. 4, the device 1 is formed of two double walled sheets 3, 4 containing in the volumes 10 between outer panels 9 and inner panels 8 a first high thermal capacity material 11. The two sheets are sealed on three edges and not sealed on edge 6. The space between the two sheets is divided into three compartments by two webs 14. Each web 14 is sealed on all its edges to one or the other inner panel 8 to define therebetween a sealed compartment 15 containing therein the second high thermal capacity material 12. The third compartment 16 defined by the two webs 14 is open at the edge 6, and is empty.

As shown in FIGS. 5 and 6, the envelope 2 may be everted or turned inside out to the configuration of FIG. 6 in which the second material 12 is on the outside enveloping the first material 11 on the inside. This embodiment may be useful when the different physical properties of materials 11 and 12 may be more useful on the outside for certain applications, making a single device more versatile.

As shown in FIG. 3, any of the compartments may be further provided with elongate fibers or strips 50 that enhance thermal properties by slowing heat transfer. Although discussed primarily for treatment of the body, the device of the invention may be used for heating or cooling any surface.

Instant hot or cold disposable packs are well known in the art. They are devices that consist of a sealed plastic bag containing separated chemicals such as, for example, a dry chemical with either a positive or a negative heat of solution and a sealed plastic bag of water. The device is activated by bursting the separating partition or inner bag of water and mixing the two ingredients to produce instant heat or cold. In an alternative embodiment of the invention, the removable inner pouch 24 may be one of these instant hot or cold packs.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A device for heating and cooling a surface, the device comprising:

a first volume, defined by a first web, containing a first high thermal capacity material;

a second volume, defined by a second web, containing a second high thermal capacity material, the first and second volumes being sealed from each other so that the first and second high thermal capacity materials cannot mix; and the first and second webs being connected to each other by a mechanical interconnection, and the second high thermal capacity material being confined wholly within said first volume.

2. The device according to claim 1, in which the second high thermal capacity material is not solid at about 0° centigrade.

3. The device according to claim 2, in which the first and second high thermal capacity materials have different heat transfer characteristics.

4. The device according to claim 2, in which the first and second walls cooperate to sealingly separate the first and second volumes from each other.

5. The device according to claim 2, wherein the second wall defines a flexible pouch having sealed therein the second high thermal capacity material, the pouch being disposed within the first volume.

6. The device according to claim 5, in which the pouch is comprised of a plurality of compartments which are hinged together.

7. The device according to claim 5, in which the first wall defines a sealable aperture for permitting removal and replacement of the pouch within the first volume.

8. A heat transfer device for heating or cooling a surface, the device comprising:

a first volume formed by at least a first liquid-impermeable sheet;

a second volume disposed within said first volume formed of at least a second liquid-impermeable sheet;

the first volume containing a first high thermal capacity material;

the second volume containing a second high thermal capacity material sealed therein such that said first and second high thermal capacity materials cannot mix; and the first and second sheets being connected to each other by a mechanical-interconnection, said second high thermal capacity material being confined wholly within said first volume.

9. The device according to claim 8, in which the first high thermal capacity material is not solid at about 0° centigrade.

10. The device according to claim 8, in which the first and second high thermal capacity materials have different heat transfer characteristics.

11. The device according to claim 8, wherein said second sheet forming the second volume is a pouch adapted for removable containment within the first volume.

12. The device according to claim 11, in which the pouch comprises at least two compartments which are hingedly connected.

13. A heat transfer device for heating and cooling a surface, comprising:

means for housing a first high thermal capacity material;

means for housing a second high thermal capacity material;

both said means cooperating so that the first and second high thermal capacity materials cannot mix;

the means for housing the first high thermal capacity material and the means for housing the second high thermal capacity material being connected to each other, the second high thermal capacity material being confined wholly within the first means for housing.

14. The device according to claim 13, wherein said first high thermal capacity material is not solid at about 0° centigrade.

15. The device of claim 14, in which the first and second high thermal capacity materials have different heat transfer characteristics.

16. A method of heating or cooling a surface, comprising:

providing a device having a first web which defines a first volume containing a first high thermal capacity material;

providing a second web to said device which defines a second volume containing a second high thermal capacity material, the first and second volumes being sealed from each other so that the first and second high thermal capacity materials cannot mix, and the second high thermal capacity material being confined wholly within said first volume;

connecting said first and second walls to each other;

exposing said device to an elevated or lowered temperature environment for a predetermined period of time; and applying the device to the surface.

17. The method according to claim 16, in which the second high thermal capacity material is not solid at about 0° centigrade.

18. The method according to claim 16, in which the first and second high thermal capacity materials have different heat transfer characteristics.

19. The method according to claim 16, wherein the second web defines a flexible pouch having sealed therein the second high thermal capacity material, the pouch being disposed within the first volume.

20. The method according to claim 19, in which the pouch is comprised of a plurality of compartments which are hinged together.

21. A device for heating and cooling a surface, the device comprising:

a first volume, defined by a first web, containing a first high thermal capacity material;

a second volume, defined by a second web, containing a second high thermal capacity material, the first and second volumes being sealed from each other so that the first and second high thermal capacity materials cannot mix;

the second web defining a flexible pouch and having sealed therein the second high thermal capacity material, the pouch being disposed within the first volume; and the first web defining a sealable aperture for permitting removal and replacement of the pouch within the first volume.

22. A heat transfer device for heating or cooling a surface, the device comprising;

a first volume formed by at least a first liquid-impermeable sheet;

a second volume disposed within said first volume formed of at least a second liquid-impermeable sheet;

the first volume containing a first high thermal capacity material;

the second volume containing a second high thermal capacity material sealed therein ouch that said first and second high thermal capacity materials cannot mix; and said second sheet forming the second volume is a pouch adapted for removable containment within the first volume.

23. The device according to claim 22, in which the pouch comprises at least two compartments which are hingedly connected.

* * * * *